United States Patent [19]

Moro et al.

[11] Patent Number: 5,468,811
[45] Date of Patent: * Nov. 21, 1995

[54] HYDROPHILIC COMPOSITE POLYMER ARTICLES FORMED FROM A SETTABLE PASTE COMPRISING A MIXTURE OF HYDROPHILIC POLYMER AND UNSATURATED MONOMER

[75] Inventors: Daniel G. Moro, Randolph; Samuel H. Ronel, Princeton; Petr Kuzma, Monmouth Junction, all of N.J.

[73] Assignee: National Patent Development Corporation, New York, N.Y.

[*] Notice: The portion of the term of this patent subsequent to Sep. 3, 2011, has been disclaimed.

[21] Appl. No.: 295,357

[22] Filed: Aug. 24, 1994

Related U.S. Application Data

[63] Continuation of Ser. No. 55,418, Apr. 29, 1993, abandoned, which is a continuation of Ser. No. 773,984, Oct. 9, 1991, abandoned, which is a continuation of Ser. No. 430,843, Nov. 2, 1989, abandoned.

[51] Int. Cl.⁶ .......................... A61L 15/16; A61L 15/07; A61L 15/24; C08F 265/06
[52] U.S. Cl. .................... 525/263; 525/265; 525/303; 525/329.4; 525/330.5; 525/374; 525/386; 523/113; 526/320; 524/460; 524/580; 424/78.06; 424/437; 424/445
[58] Field of Search ............... 424/78.08, 78.06, 424/445, 447; 525/303, 374, 386, 263, 265, 329.4, 330.5; 526/320; 523/113; 524/460, 580

[56] References Cited

U.S. PATENT DOCUMENTS

| | | | |
|---|---|---|---|
| 2,120,006 | 6/1938 | Strain | 526/320 |
| 3,868,447 | 2/1975 | Kliment | 426/221 |
| 3,941,858 | 3/1976 | Shepherd et al. | 525/303 |
| 4,038,264 | 7/1977 | Rostoker et al. | 526/320 |
| 4,192,827 | 3/1980 | Mueller et al. | 525/123 |
| 4,272,518 | 6/1981 | Moro et al. | 424/78.02 |
| 4,563,184 | 1/1986 | Korol | 604/368 |
| 4,769,400 | 9/1988 | Geist et al. | 526/320 |
| 5,044,266 | 6/1991 | Moro et al. | 96/446 |

FOREIGN PATENT DOCUMENTS 2157300  10/1985  United Kingdom.

*Primary Examiner*—Peter F. Kulkosky
*Attorney, Agent, or Firm*—Howson and Howson

[57] ABSTRACT

Hydrophilic composite polymer articles are provided which comprise at least one hydrophilic polymer in a powder form and one or more liquid components of which at least one is hydrophilic and which can be polymerized with said hydrophilic polymer. This composition is produced from a homogeneously mixed paste which can be molded or cast into a desired shape which will subsequently set. The resulting article has a shape-retaining, non-tacky flexible consistency which allows the shape to be further modified, if necessary.

Such object can be then cured by any of the conventional curing methods to retain its shape permanently. The final properties of the composite can be tailored to suit the final application by using fillers or modifiers. In the medical field, such articles can be utilized as a sustained release devices as they can be loaded with the desired therapeutic drugs. These articles can be made non-toxic and biocompatible and used as prosthetic devices.

The final cured article can be modified further by polishing, drilling, cutting, etc. When exposed to moisture or a humid environment, the article will become partially hydrated with a resultant softer surface yet retain good mechanical strength.

21 Claims, No Drawings

HYDROPHILIC COMPOSITE POLYMER ARTICLES FORMED FROM A SETTABLE PASTE COMPRISING A MIXTURE OF HYDROPHILIC POLYMER AND UNSATURATED MONOMER

This is a continuation of prior application Ser. No. 08/055,418, filed on Apr. 29, 1993, abandoned which is a continuation of prior application Ser. No. 07/773,984, filed on Oct. 9, 1991, now abandoned, which is a continuation of application Ser. No. 07/430,843, filed on Nov. 2, 1989, now abandoned.

CROSS-REFERENCE TO RELATED PATENT APPLICATIONS

The present patent application has subject matter related to the disclosure of U.S. Pat. No. 5,045,266, (filed concurrently herewith).

BACKGROUND OF THE INVENTION

This invention relates to novel hydrophilic polymeric materials which are water-insoluble and water-swellable and which can be shaped effectively both before and after curing economically by conventional processing techniques.

In many instances in the health field it is desirable to shape an article so as to accurately mimic a bodily cavity or so as to form a perfect fit for better comfort and biocompatibility. In most conventional methods a negative imprint is first formed by filling the cavity with moldable material, removing it from the cavity and subsequently using it to prepare a mold for molding the desired shaped article(s). This is quite costly and extremely time consuming, especially when suitable apparatus for preparing the mold is not at hand. Further, it is sometimes difficult to do, especially when the cavity opening is smaller than the parameters of the actual cavity. In some medical applications, as in the case of bone prosthesis, etc., it may be advantageous to form the final article in situ. This may be impossible with most thermosetting plastics or with other materials which cure to rigid, inflexible shaped articles and do not form a settable paste intermediate stage.

Further, it is known to treat wounds, especially burned tissue surfaces, with a settable paste which may have medicinally active ingredients therein. Such paste and procedures are described in U.S. Pat. No. 4,272,518 which utilizes a hydrophilic polymer and an inert, normally-liquid organic vehicle having a relatively high boiling point. The resulting paste possesses a setting time period no greater than about one hour, and a working time period which is sufficient to permit an operator (e.g., clinician, nurse, doctor) to apply the paste to the wound and thereby obtain an occlusive film dressing. The preferred polymer employed therein is 2-hydroxyethyl methacrylate polymer and the preferred solvent is polyethylene glycol of 400–800 molecular weight.

while representing an advance in the art, such materials can evidence certain disadvantages, e.g., they are not readily curable and thus do not provide long term stable physical properties such as shape retention when exposed to solvents.

SUMMARY OF THE INVENTION

The present invention provides novel compositions and processes to form articles from novel settable paste which can be cured when removed from a mold to a hard or semi-hard state.

Accordingly, at least one water-insoluble, water-swellable, hydrophilic polymer (e.g., poly[2-hydroxyethyl methacrylate]) which is in a finely divided powder form, is with at least one hydrophilic solvent/plasticizer which is capable of vinyl polymerization, (e.g., 2-hydroxyethyl methacrylate monomer). When a solvation or plasticization occurs, the components will set, resulting in rubbery shape-retaining article which can be further cured into a stable, insoluble, hydrophilic hard or semi-hard shape.

It is important that the two basic components are hydrophilic, as the hydrophilic interaction is the basis for setting, (such as hydrogen bonding).

In order to impart desired properties, i.e., hardness, softness, different degree of hydrophilicity, etc., other components as hereinlater described, can be incorporated therein.

For lesser hydrophilicity the powderized polymer can contain more hydrophobic moiety or the powder can be made from a copolymer of hydrophilic and hydrophobic components.

Similarly, the plasticizer can be a monomer of lower hydrophilicity, (e.g., hydroxypropyl methacrylate) or a mixture of hydrophilic with hydrophobic monomers, (e.g., 2-hydroxypropyl methacrylate with a small amount of methyl methacrylate). It is important to note, however, that too much of hydrophobic components will disrupt the hydrophilic interactions needed for the paste to set.

The final properties can be also affected by the use of a coplasticizer which is not polymerizable. Such coplasticizer will affect hardness and setting time.

It is preferred, but it is not required, that a small amount of crosslinking agent is added so the final product is three dimensional and its components cannot be separated, i.e., with solvents.

To facilitate the final curing step it may be necessary to add an initiator of polymerization. The choice of an initiator will depend on the curing method.

The final properties can also be modified with the use of fillers and the like.

Also, as the final product will have a controlled degree of hydrophilicity, i.e., it will behave as a hydrogel, this property can be utilized for the controlled release of active substances, such as drugs, fragrances, flavors, antimicrobials, biologically active factors, and the like.

It is deemed advisable at this time to set forth certain definitions which will facilitate an understanding the invention as described herein.

The term "working time", as used herein, is the maximum period of time during which the novel paste (in the mixing vessel), is in a sortable and usable state. After the working time period is exceeded (in the mixing vessel) the paste "hardens" and "sets", the shaped articles therefrom are either non-attainable or very poor in characteristics. One can liken such hardened or set paste with a mixture of plaster of paris and water which has remained in the mixing vessel beyond its settable period.

The term "setting time", as used herein, is the period of time required commencing upon the shaping or molding of the novel paste, to form a non-tacky, shaped or molded article or occlusive film.

The term "curing time", as used herein, is the time utilized subsequent to "hardening" or "setting" to cure the "set" article by conventional curing methods, i.e., heat, gamma irradiation, UV light, etc.

The term "composite", as used in conjunction with the set" or "cured" hydrophilic polymer articles herein, is used inasmuch as such articles may be made up from distinct, albeit similar, parts, e.g., HEMA powder and HEMA monomer, as well as fillers and other ingredients, and combine the typical or essential characteristics of the parts of said composite.

The term "paste", as used herein, relates to a soft plastic, shapable, moldable mixture comprised of the "composite" parts. It is most preferably homogenous.

DESCRIPTION OF THE PREFERRED EMBODIMENTS

Hydrophilic Polymer Component

The hydrophilic polymeric component useful in the practice of the invention is a hydrophilic, water-insoluble, water-swellable, generally at least slightly crosslinked, and preferably non-toxic, particulate solid. Poly(2-hydroxyethylmethacrylate), i.e., (poly HEMA), is preferred. However, other hydroxyalkyl acrylates or hydroxyalkyl methacrylates can be employed. Also, other hydrophilic polymers such as polyacrylamides, polymethacrylamides, substituted polyacrylamides or polymethacrylamides, polyvinylpyrrolidone, polymethacrylic acid, polyacrylic acid, polyglycol acyrlates and methacrylates, etc., can be used.

Typical of the classes of monomers useful in the preparation of the hydrophilic polymer component are the hydroxyalkyl 2-alkenoates such as the hydroxy($C_2$–$C_4$alkyl) methacrylates and the hydroxy($C_2$–$C_4$alkyl) acrylates; the hydroxy($C_2$–$C_4$ alkoxy$C_2$–$C_4$alkyl) alkenoates, e.g., 2-hydroxyethoxyethyl acrylate and methacrylate the alkoxy($C_2$–$C_4$alkoxy$C_2$–$C_4$alkyl) alkenoates, e.g., methoxyethoxyethyl acrylate and methacrylate; the N-vinylpyrrolidones including the mono- and di-($C_1$–$C_4$alkyl)-N-vinylpyrrolidones; the 2-alkenamides including the N-($C_1$–$C_4$alkyl)-2-alkenamides and $N_1$N-di($C_1$–$C_4$alkyl)-2-alkenamides such as the N-($C_1$–$C_4$alkyl) acrylamides, the N-($C_1$–$C_4$alkyl)-methacrylamides, the $N_1$N-di($C_1$–$C_4$alkyl)acrylamides, and $N_1$N-di($C_1$–$C_4$alkyl) methacrylamides; the vicinal-epoxyalkyl 2-alkenoates, including the vicinal-epoxy($C_2$–$C_4$alkyl) methacrylates, and the vicinal-epoxy($C_2$–$C_4$alkyl) acrylates; with or without other monomers or modifiers such as the alkyl alkanoates, e.g., methyl butyrate, butyl acetate, etc.; the dialkylaminalkyl 2-alkenaotes, e.g., diethylaminoethyl methacrylate; the vinylpyridines; the lower alkoxy (lower alkyl) methacrylates, e.g., ethoxyethyl methacrylate; and mixtures of the illustrative foregoing compounds.

Preferred monomers useful in the preparation of polymers include, by way of examples, 2-hydroxyethyl acrylate; 2-hydroxyethyl methacrylate; diethylene glycol monoacrylate; diethylene glycol monomethacrylate; 2-hydropropyl acrylate; 2-hydroxypropyl methacrylate; 3-hydroxypropyl acrylate; 3-hydroxpropyl methacrylate; dipropylene glycol monomethacrylate; dipropylene glycol monoacrylate; acrylamide; N-methylmethacrylamide; N,N-dimethacrylamide; methylvinylpyrrolidone; glycidyl methacrylate; 2,3-dihydroxypropyl methacrylate; and the like. Most preferred is 2-hydroxyethyl methacrylate, (HEMA monomer).

Particularly suitable hydrophilic polymers are those which are characterized by being made from at least 50 mol percent, preferably at least 80 mol percent, of a monomer of the formula:

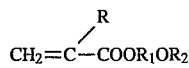

wherein R is hydrogen or methyl; wherein $R_1$ is $C_2$–$C_4$alkylene, e.g., ethylene, propylene or butylene; and wherein $R_2$ is hydrogen or $C_1$–$C_4$alkyl, or $C_1$–$C_4$alkoxy$C_1$–$C_4$alkyl. The resulting hydrophilic polymer will thus be characterized by at least 50 mol percent, preferably at least 80 mol percent, of the following recurring unit:

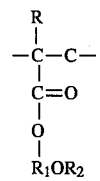

wherein R, $R_1$ and $R_2$ have the aforesaid assigned values.

As an example of a preferred polymer for the present invention is a hydroxyethyl methacrylate polymer prepared by aqueous bulk polymerization using ultra-pure monomers characterized by a very low concentration of impurities conducive to crosslinking reactions, see U.S. Pat. No. 3,963, 685. The above polymers can be prepared under "clean conditions" easily purified from residual monomers, and easily reduced to powders of the desired particle size.

The molecular weight of the hydrophilic polymer desirably is of at least about 50,000 and preferably above about 250,000 and upwards to several million. Molecular weights over the entire range and even outside these limits may be tolerated providing the hydrophilic polymers meet the characteristics noted in this specification. Hydrophilic polymer in particulate form is employed in the preparation of the novel pastes. Desirably, the polymer is micropulverized to particles of a dimension smaller than 50 mesh, preferably below 100 mesh (Tyler sieve). In one desirable embodiment, the bulk density of the particulate hydrophilic powder is at least about 0.6 gram/cc, and preferably at least about 0.7 gram/cc. Polymers 2-hydroxyethyl methacrylate in the 100 to 378 mesh range are particularly suitable in the practice of preferred aspects of the invention.

Solvent/Plasticizer—Polymerizable Hydrophilic Monomer Component

The water-insoluble water swellable hydrophilic polymers described in "Hydrophilic Polymer Component" supra are preferably capable of forming with the hydrophilic monomer component as described herein as a novel settable paste.

Typical of the classes of monomers which can be used as the hydrophilic monomer component are the hydroxyalkyl 2-alkenoates such as the hydroxy($C_2$–$C_4$alkyl) methacrylates and the hydroxy($C_2$–$C_4$alkyl) acrylates; the hydroxy($C_2$–$C_4$alkoxy$C_2$–$C_4$alkyl) alkenoates, e.g., 2-hydroxyethoxyethyl acrylate and methacrylate; the alkoxy($C_2$–$C_4$alkoxy$C_2$–$C_4$alkyl) alkenoates, e.g., methoxyethoxyethyl acrylate and methacrylate; the N-vinylpyrrolidones including the mono- and di-($C_1$–$C_4$alkyl)-N-vinylpyrrolidones; the 2-alkenamides including the N-($C_1$–$C_4$alkyl)-2-alkenamides and $N_1$N-di($C_1$–$C_4$alkyl)-2-alkenamides such as the N-($C_1$–$C_4$alkyl) acrylamides, the N-($C_1$–$C_4$alkyl)-methacrylamides, the $N_1$N-di($C_1$–$C_4$alkyl)acrylamides, and $N_1$N-di($C_1$–$C_4$alkyl) methacrylamides; the vicinal-epoxyalkyl 2-alkenoates, including the vicinal-epoxy($C_2$–$C_4$alkyl) methacrylates, and the vicinal-epoxy($C_2$–$C_4$alkyl) acrylates; with or without other monomers or modifiers such as the alkyl alkanoates, e.g., butyrate, butyl acetate, etc.; the dialkylaminalkyl 2-alkenaotes, e.g., diethylaminoethyl methacrylate; the vinylpyridines; the lower alkoxy (lower alkyl) methacrylates, e.g., ethoxyethyl methacrylate; and mixtures of the illustrative foregoing compounds.

Preferred monomers include, by way of examples, 2-hydroxyethyl acrylate; 2-hydroxyethyl methacrylate; diethylene glycol monoacrylate; diethylene glycol monomethacrylate; 2-hydropropyl acrylate; 2-hydroxypropyl methacrylate; 3-hydroxypropyl acrylate; 3-hydroxpropyl methacrylate; dipropylene glycol monomethacrylate; dipropylene glycol monoacrylate; acrylamide; N-methylmethacrylamide N,N-dimethacrylamide; methylvinylpyrrolidone; glycidyl methacrylate; 2,3-dihydroxypropyl methacrylate; and the like. Most preferred is 2-hydroxyethyl methacrylate; (HEMA monomer).

Coplasticizer—Hydrophilic Solvent Component

A solvent may be employed, if desired, in conjunction with the hydrophilic monomer component when forming the settable paste containing the hydrophilic polymer of the present invention.

The solvents contemplated herein are inert, non-toxic, normally-liquid, water-miscible organic liquids as exemplified by water-miscible polar compounds including the glycols such as ethylene glycol; propylene glycol; dipropylene glycol butanediol-1,3; butanediol-1,4; hexanediol-2,5; 2-methyl-2,4-pentanediol; heptanediol-2,4; 2-ethyl-1,3-hexanediol; diethylene glycol; triethylene glycol; tetraethylene glycols; and the higher polyethylene glycols and other water-soluble oxyalkylene homopolymers and copolymers having a molecular weight up to 2000, and higher, desirably up to 1600, e.g., hydroxy-terminated polymers of ethylene oxide having average molecular weights of 200–1000, the water-soluble oxyethyleneoxypropylene polyol (especially glycol) polymers having molecular weights up to about 1500, desirably up to about 1000, propylene glycol monoethyl ether; monoacetin; glycerins; tri(hydroxyethyl) citrate; ethylene glycol monomethyl ether; ethylene glycol monoethyl ether; di(hydroxypropyl) oxalate; hydroxypropyl acetate; glyceryl triacetate; glyceryl tributyrate; liquid sorbitol ethylene oxide adducts; liquid glycerins ethylene oxide adducts; diethylene glycol monomethyl ether; diethylene glycol monoethyl ether; and ethylene glycol diacetate.

Water, either alone or in combination with the above solvents, is contemplated by the present invention.

The proportion of the hydrophilic polymer component to the monomer component or mixture of monomer component and solvent component will be governed, to a significant extent, by variables such as the hydrophilic polymer of choice, the particle size of the polymer, the molecular weight of the polymer, the hydrophilic monomer of choice, the molecular weight of the monomer, the organic liquid of choice, the molecular weight of the organic liquid, the particular hardening time, setting time, and/or working time which is desired, and other factors. As will be apparent from a consideration of the working Examples, the mixing of the components together to obtain a uniform paste is relatively easy to accomplish. Taking into account the above factors, one skilled in the art can readily determine the optimum amount of particulate hydrophilic polymer relative to monomer or monomer plus solvent which is necessary to yield a paste possessing a setting time of up to about 1 hour, preferably less than one hour, e.g., less than 45–50 minutes, and a working time which is sufficient to allow an operator to obtain by suitable means an integral, homogeneous, non-tacky shaped article of sufficient mechanical strength and other suitable properties. In the practice of preferred aspects of the invention novel pastes are prepared by using polymer to monomer or monomer plus solvent ratios (by weight) of from about about 0.53:1 to about 2.0:1, preferably from about 0.85:1 to below about 1.75:1, more preferably still from about 0.85:1 to about 1.55:1, and most preferably from above about 0.85:1 to below about 1.45:1.

If the mixture of a hydrophilic polymer with a hydrophilic monomer results in a composite polymer product which is too hydrophilic, it may be necessary to employ a sufficient amount, generally up to 50 mol percent, of a copolymerization monomer which will render the composite less hydrophilic. Such comonomers include, by way of illustrations, methyl acrylate; ethyl acrylate; propyl acrylate; butyl acrylate; 2-ethylhexyl acrylate; ethyl methacrylate; butyl methacrylate; methoxyethyl acrylate; methoxyethyl methacrylate; and ethoxyethyl methacrylate.

Crosslinking Agent

Desirably, small amounts of cross-linking agent or other ingredient either inherently contained in the monomer and/or added thereto, or other means, e.g., photo-polymerization, can be employed to impart a three-dimensional, water-insoluble, structure to the resulting hydrophilic composite product.

The amount of crosslinking agent employed herein is usually kept low, i.e., amounts of from about 0.05 to 10.0 weight percent. Such amounts will be governed by the effectiveness or activity of such agent.

Illustrative crosslinking agents include ethylene glycol diacrylate; ethylene glycol dimethacrylate; 1.2,-butylene dimethacrylate; 1,3-butylene dimethacrylate; 1,4-butylene dimethacrylate; propylene glycol diacrylate; propylene glycol dimethacrylate; diethylene glycol dimethacrylate; dipropylene glycol dimethacrylate; divinylbenzene; divinyltoluene; divinyl tartrate; triallyl melamine; glycerins trimethacrylate; diallyl maleate; diallyl monoethylene glycol citrate; allyl vinyl maleate; diallyl itaconate; ethylene glycol diester of itaconic acid; divinylsulfone; triallyl phosphite, polyester of maleic anhydride with triethyleneglycol; polyallyl glucose; pentaallyl sucrose; sucrose diacrylate; glucose dimethacrylate; divinyl citraconate; dially fumarate; glycidyl methacrylate; allyl methacrylate; and vinyl methacrylate. The crosslinking agent(s) usually, but not necessarily, have at least two ethylenically unsaturated double bonds. The most suitable crosslinking agents are dimethacrylates and/or diacrylates of the ethylene glycol homologues, including mono- di-, tri-, tetra-, poly-, etc. ethylene glcyol. Various other bi- and poly-functional ethylenically unsaturated monomers are also appropriate as indicated above.

Polymerization (Curing) and Initiators of Polymerization

The novel composite articles of the present invention can be cured by well known polymerization techniques using convention free radical initiators. The polymerization reaction can be carried out at over a wide temperature range, e.g., 20° to 105° C., frequently 35° to 40° C. to 90° C. A catalytically significant quantity of a free-radical catalyst is employed, e.g., from 0.05 to 1 percent based on the total weight of polymerizable monomers. Typical catalysts include t-butyl peroctoate, isopropyl percarbonate, and benzoyl peroxide. Irradiation, e.g., by ultraviolet light or gamma rays, can also be employed to catalyze the polymerization reaction.

The type and amount of the free-radical initiator used to effect the polymerization is not critical and will be obvious to those versed in the art. The only limitations imposed on the choice of the initiator is its solubility in the final (i.e., monomer(s), solvent(s) and active ingredients) mixture and its ability to initiate the polymerization at temperatures acceptable for the given ingredient.

Fillers

Fillers can be, for example, silica, e.g., Aerosil 380, diatomaceous earth, Fullers earth, clays, talc, mica, bentonite, alumina, wood flour, activated carbon and the like. Fibers natural or man-made are suitable fillers as well.

Also contemplated herein are materials prepared from the hydroxy lower alkylcelluloses, cross-linked or otherwise, and rendered insoluble in water but still retaining their hydrophilicity and solubility in organic solvents such as methanol, e.g., from hydroxyethylcellulose, hydroxypropylcellulose or carboxymethylcellulose; the partially crosslinked natural polymers such as guar gum, karaya gum, gelatin, e.g., partially crosslinked with formaldehyde or glutaraldehyde and salts of alginic acid which are rendered water insoluble.

Release of Active Ingredients or Fragrances

As mentioned, the hydrophilic composite articles of the present invention lend themselves to the release of "active" ingredients contained therein.

Medicinally active ingredients such as germicides, fungicides, antibiotics, analgesics, or the like may be utilized by having the medicinally active ingredient suspended, entrapped in, or admixed with the polymer or in the novel paste. Examples of such medicinally active ingredients include silver sulfadiazine; benzocaine; xylocaine; aspirin; sodium omadine (a derivative of 1-hydroxypyridine-2-thione); hexachlorophene; bacitracin; cortisone; trimethylbenzylammonium chloride; cetyl pyridinium chloride; penicillin; Aueromycin (chlorotetracycline); chloromycetin (chloromphenicol).

The, active ingredient may also be a fragrance, essence or flavor. Typical examples of such materials includes lemon oil, strawberry, orange oil, anethole, citral biacetyl, menthol, anise, amyl acetate, ethyl acetate, lavender oil, pine, blue spruce, apple, spearmint, peppermint, spice mint, peach, attar of roses, apple (International Flavors and Fragrances #58125), pine (IFF-4276-X), spearmint (IFF V 30549), lime (IFF 3117 W), spice-mint (Gentry #401283-00), carnation-peach (Gentry #401186-00), lemon-verbenna (Ungerer C-454), soap fragrance (Roue Bertrand DuPont D 723), melon (American Aromatics #12), (Felton International): floral bouquet #221, leather musk bouquet #323, cream bouquet #800, rose bouquet #593A, green apple bouquet #503, pine bouquet #740A, strawberry #863.

There can also be added bactericidal agents, e.g., benzalkonium chloride, disinfecting agents, insect repellants, e.g., N,N-diethyl-m-toluamide, and pyrethrum flowers, etc.

There can be added soluble or insoluble dyes and pigments, e.g., FD&C yellow #5, D&C Red #9 (Thomasset Colors), D&C mint green (Pylam Products Co.), mercadium red light GP (Hercules), C.P. medium yellow (Hercules), titanium dioxide (Unitane-American Cyanamide), carbon black (Konstamm).

Unless otherwise indicated, all parts and/or percentages throughout this application are by weight.

The terms "polymer" and "copolymer" are used interchangeably herein and designate polymeric products obtained by the polymerization of two or more polymerizable monomers and/or polymerizable polymers and/or mixtures thereof.

The term "fragrance" as used in this application and claims is used in a generic sense to include not only fragrances, but also perfume oils, essence, flavors, various cuts, distillates and fractions which give aromas and flavors, and the like.

Utility of the Articles

The hydrophilic composite articles produced in accordance with the present invention can be shaped and have their final properties tailored to suit the final application by using the fillers and active materials described herein.

Typical end-uses are swellable washers and O-rings; fragrance emitting shaped articles; wound or burn dressings which may contain one or wore active medicinal agents; sustained release devices which conform to body contours and which are loaded with desired therapeutic drugs; such articles can also be made non-toxic and biocompatible and used as prosthetic devices, diaphragms, etc.

In the following Examples which illustrate the preferred embodiments of the present invention, pastes are prepared by mixing the components utilized homogeneously. The hydrophilic polymer to plasticizer ratios utilized are as hereinbefore set forth. Other ingredients, i.e., coplasticizers, fillers and active ingredients are added in amounts suitable to illustrate the specific needs. These ingredients are added in amounts which would not interfere with the subsequent curing step.

The homogeneous paste resulting from the mixing step is formed into a desired shape by filling a bodily cavity, molding, extruding, casting, injection molding, etc., and allowed to set. When fully set, it retains its shape and has rubbery characteristics. In this state it can be shaped further (if needed) by cutting, punching holes, etc.

In the next step, it is cured to render it a permanent shape as described previously. The cured article can be finished or refined even further by polishing, drilling, etc.

EXAMPLE 1

The following ingredients were mixed homogeneously together in a suitable vessel to form a paste:

3.2 g polyHEMA powder 2.8 g HEMA monomer 0.28 g ethylene glycol dimethacrylate 0.014 g percadox 16 (Noury initiator)

The resulting paste was cast on a glass plate as a thin film and allowed to set. The setting time was 10 minutes.

After the film was set, it was peeled off the plate and placed on a TEFLON foil. 2×2 cm squares were cut out and placed in the oven at 90° C. for 30 minutes for curing. Cured squares were then placed in water. After hydrations, strong and flexible membranes saturated with water resulted.

EXAMPLE 2

The following ingredients were mixed homogeneously together in a suitable reaction vessel to form a paste:

6.0 g polyHEMA powder 4.0 g HEMA monomer 0.02 g Benzoin methyl ether (UV initiator)

0.04 g polyethyleneglycol-400-dimethacrylate 1.0 g polyethylene glycol 400

0.1 g peppermint oil

After mixing, the paste was extruded in the form of "spaghetti" on a TEFLON coating foil and allowed to set. The setting time was 16 minutes. After setting, the spaghetti was cut into small pellets. The pellets were then exposed to an ultraviolet light for 10 minutes. The cured pellets were semi-soft, emitting a mint fragrance when exposed to ambient temperatures. Such a product can be used for a fragrance

EXAMPLE 3

The following ingredients were mixed homogeneously together in a suitable reaction vessel to form a paste:

4.0 g polyHEMA powder 1.0 g polyvinylpyrrolidone-iodine complex (Aldrich)

3.0 g HEMA monomer 0.015 g ethylene glycol dimethacrylate 0.015 g t-butylperoctate (Lucidol)

1.0 g polyethyleneglycol 400

The paste was cast on a glass plate as a thin film. The film set in 15 minutes. After setting, the film was peeled off the glass and placed on a TEFLON backed foil. The film was cut into smaller strips which were then placed in an oven at 85° C. for 30 minutes. Cured strips were then washed and hydrated in a 0.9% saline solution. The hydrated strips (strong and flexible) were then packaged individually in sealed plastic bags to retain moisture. This product is suitable as a wound dressing as discussed more fully in U.S. Pat. No. 4,272,518.

EXAMPLE 4

The following ingredients were mixed homogeneously together in a suitable vessel to form a paste:

5.0 g polyHEMA powder 1.0 g CAB-O-SIL (FUMED SILICA, CABOT CORP.)

3.5 g hydroxypropyl methacrylate 0.035 g polyethyleneglycol-400-dimethacrylate 0.02 g t-butylperoctate (LUCIDOL)

The resulting paste was cast as a film of about 2 mm thickness on a glass plate and allowed to set. The setting time was 18 minutes. The film was then removed and rings of different sizes were cut out. The rings were then placed between TEFLON backed glass plates and cured in the oven at 90° C. for 45 minutes. The cured rings were then placed in the water to hydrate. Hydrated rings were flexible and strong. This property can be effectively utilized in self-sealing washers and seals. When such a seal was placed dry in a wet environment, it hydrated and expanded to form an effective seal.

What is claimed is:

1. A process for producing a stable, hard or semi-hard, shaped composite article which comprises:

(a) forming a homogeneous, moldable intermediate material which material remains stable for a significant period of time without becoming hard; comprising a mixture consisting essentially of (1) a particulate, water-insoluble, water-swellable hydrophilic (co-)polymer formed from a monomer selected from the group consisting of a hydroxyalkyl 2-alkenoate, a hydroxy-($C_2$–$C_4$alkoxy$C_2$–$C_4$alkyl) alkenoate, an alkoxy($C_2$–$C_4$alkoxy$C_2$–$C_4$alkyl) alkenoate, a N-($C_1$–$C_2$alkyl)-2-alkenamide, a N,N-di($C_1$–$C_4$alkyl)-2-alkenamide, and mixtures thereof; (2) a polymerizable monoethylenically unsaturated monomer selected from the group consisting of a hydroxyalkyl 2-alkenoate, a hydroxy($C_2$–$C_4$alkoxy$C_2$–$C_4$) alkenoate, an alkoxy($C_2$–$C_4$alkoxy$C_2$–$C_4$alkyl) alkenoate, a N-vinylpyrrolidone, a N-($C_1$–$C_4$alkyl)-2-alkenamide, a N,N-di($C_1$–$C_4$alkyl)-2-alkenamide, and mixtures thereof, wherein said polymer (1) and monomer (2) are in a ratio of between 1:2 and 2:1 by weight; (3) a cross-linking monomer agent in an amount of from about 0.05 to 10 weight percent based on the total weight of the polymer and monomer in said paste; and (4) a free radical initiator;

said material characterized by a setting time of up to about one hour and remaining in a moldable form for a significant period of time in order to provide a working time sufficient to form the material into a desired shape;

(b) molding said material to a desired shaped form;

(c) allowing said shaped form to set; and (d) curing said shaped form whereby there is obtained a homogeneous, stable hard or semi-hard shaped article.

2. A homogeneous, moldable material comprising a mixture consisting essentially of:

(a) a particulate, water-insoluble, water-swellable hydrophilic (co-)polymer formed from a monomer selected from the group consisting of a hydroxyalkyl 2-alkenoate, a hydroxy-($C_2$–$C_4$alkoxy$C_2$–$C_4$alkyl) alkenoate, an alkoxy-($C_2$–$C_4$alkoxy$C_2$–$C_4$alkyl) alkenoate, a N-($C_1$–$C_4$alkyl)-2-alkenamide, a N,N-di($C_1$–$C_4$alkyl)- 2-alkenamide, and mixtures thereof;

(b) a polymerizable monoethylenically unsaturated hydrophilic monomer selected from the group consisting of a hydroxyalkyl 2-alkenoate, a hydroxy($C_2$–$C_4$alkoxy$C_2$–$C_4$) alkenoate, an alkoxy($C_2$–$C_4$alkoxy$C_2$–$C_4$alkyl) alkenoate, a N-vinylpyrrolidone, a N-($C_1$–$C_4$alkyl)-2-alkenamide, a N,N-di($C_1$–$C_4$alkyl)-2-alkenamide, and mixtures thereof, wherein said polymer (1) and monomer (2) are in a ratio of between 1:2 and 2:1 by weight;

(c) a crosslinking monomer agent in an amount of from about 0.05 to 10 weight percent based on the total weight of the polymer and monomer in said paste;

(d) a free radical initiator; and (e) an optional hydrophilic solvent, said material characterized by the ability to form an intermediate which retains a desired shape without polymerization and remains in a moldable form for a significant period of time without hardening, and by susceptibility to subsequent curing into a hardened shape.

3. The moldable material of claim 2 wherein said hydrophilic solvent is employed with said monomers and is an inert, normally liquid, water-miscible organic liquid or water.

4. The moldable material of claim 2 wherein said polymer is characterized by at least 50 mol percent of the following recurring unit

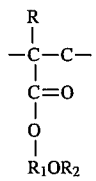

wherein R is hydrogen or methyl, wherein $R_1$ is $C_2$–$C_4$alkylene, and wherein $R_2$ is hydrogen, $C_1$–$C_4$alkyl or $C_1$–$C_4$alkoxy$C_1$–$C_4$alkyl.

5. The moladable material of claim 2 wherein said monomer is 2-hydroxyethyl methacrylate.

6. The moldable material of claim 3 wherein said hydrophilic solvent is ethylene glycol; propylene glycol; dipropylene glycol; butanediol-1,3, butanediol-1,4; hexanediol- 2,5; 2-methyl-2,4-pentanediol; heptanediol-2,4; 2-ethyl-1,3-hexanediol; diethylene glycol; triethylene glycol tetraethylene glycol; a higher polyethylene glycol or other water-soluble oxyalkylene homopolymer or copolymer having a molecular weight up to about 2000; a water-soluble oxyethyleneoxypropylene polyol polymer having a molecular weight up to about 1500; propylene glycol monoethyl ether; monoacetin; glycerine; tri(hydroxyethyl)citrate; ethylene glycol; monomethyl ether; ethylene glycol monoethyl ether; di(hydroxypropyl)oxalate; hydroxypropyl acetate; glyceryl triacetate; glyceryl tributyrate; a liquid sorbitol ethylene oxide adduct; a liquid glycerine ethylene oxide adduct; diethylene glycol monomethyl ether; diethylene glycol monoethyl ether; or ethylene glycol diacetate.

7. The process of claim 1 wherein said polymer is characterized by at least 50 mol percent of the following recurring unit

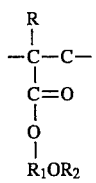

wherein R is hydrogen or methyl, wherein $R_1$ is $C_2$–$C_4$alkylene, and wherein $R_2$ is hydrogen, $C_1$–$C_4$alkyl or $C_1$–$C_4$alkoxy$C_1$–$C_4$alkyl.

8. The process of claim 1 wherein said monomer is 2-hydroxyethyl methacrylate.

9. The process of of claim 1 wherein a hydrophilic solvent is employed with said monomers, said solvent being an inert, normally-liquid, water-miscible organic liquid or water.

10. The moldable material of claim 2, wherein said polymer has a molecular weight of at least about 50,000.

11. The moldable material of claim 10, wherein R is methyl, wherein $R_1$ is ethylene, and $R_2$ is hydrogen.

12. The moldable material of claim 2, wherein said polymer is a polymer of 2-hydroxyethyl methacrylate.

13. The moldable material of claim 5, wherein said material contains a filler.

14. The moldable material of claim 2, wherein the material contains a major amount, by weight, of polymer based on the total weight of polymer plus monomer.

15. A stable, hard or semi-hard shaped composite article prepared by curing the moldable material of claim 2.

16. The process of claim 1, wherein R is methyl, wherein $R_1$ is ethylene, and $R_2$ is hydrogen.

17. The process of claim 1, wherein said polymer is a polymer of 2-hydroxyethyl methacrylate.

18. The moldable material according to claim 2 wherein the crosslinking agent is selected from the group consisting of dimethacrylates and diacrylates of ethylene glycol homologues.

19. The moldable material according to claim 2 wherein the free radical initiator is selected from the group consisting of t-butyl peroctoate, isopropyl percarbonate and benzoyl peroxide.

20. The process according to claim 1 wherein the crosslinking agent is selected from the group consisting of dimethacrylates and diacrylates of ethylene glycol homologues.

21. The process according to claim 1 wherein the free radical initiator is selected from the group consisting of t-butyl peroctoate, isopropyl percarbonate and benzoyl peroxide.

* * * * *

UNITED STATES PATENT AND TRADEMARK OFFICE
CERTIFICATE OF CORRECTION

PATENT NO. : 5,468,811
DATED : November 21, 1995
INVENTOR(S) : Daniel G. Moro, Samuel H. Ronel, and Petr Kuzma It is certified that error appears in the above-indentified patent and that said Letters Patent is hereby corrected as shown below:

Col. 2, line 51, delete "sortable" and insert thereof -- settable --.

Col. 4, line 44, delete "378" and insert thereof -- 375 --.

Col. 5, line 40, delete "glycerins" and insert thereof -- glycerine --.

Col. 5, line 44, delete "glycerins" and insert thereof -- glycerine --.

Col. 6, line 6, delete "0.53:1" and insert thereof -- 0.5:1 --.

Col. 6, line 37, delete "glycerins" and insert thereof -- glycerine --.

Col. 10, line 63, Claim 5, delete "moladable" and insert thereof -- moldable --.

Signed and Sealed this

Thirtieth Day of April, 1996

Attest:

BRUCE LEHMAN

Attesting Officer

Commissioner of Patents and Trademarks